US00PP12261P2

(12) United States Plant Patent
Sorensen

(10) Patent No.: US PP12,261 P2
(45) Date of Patent: Dec. 11, 2001

(54) OSTEOSPERMUM PLANT NAMED 'AKSINTO'

(75) Inventor: Carl Aksel Kragh Sorensen, Aabyhoj (DK)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/422,168

(22) Filed: Oct. 22, 1999

(51) Int. Cl.[7] ..... A01H 5/00
(52) U.S. Cl. ..... Plt./360

(58) Field of Search ..... Plt./360

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Osteospermum plant named 'Aksinto', characterized by its compact and mounding growth habit; very uniform plant habit; freely flowering habit with numerous inflorescences per plant; light lavender ray florets and blue purple disc florets; short peduncles, flowers held just above and beyond the foliage; and good high temperature tolerance.

1 Drawing Sheet

BACKGROUND OF THE INVENTION

The present invention relates to a new and distinct cultivar of Osteospermum plant, botanically known as *Osteospermum ecklonis*, and hereinafter referred to by the cultivar name Aksinto.

The new cultivar is a product of a planned breeding program conducted by the Inventor in Aabyhoj, Denmark. The objective of the breeding program was to create new Osteospermum cultivars with interesting ray floret colors and heat-tolerance.

The new cultivar originated from a cross made by the Inventor of a proprietary selection of *Osteospermum ecklonis* identified as code number 9631 as the female, or seed, parent and the *Osteospermum ecklonis* cultivar Dondo, disclosed in U.S. Plant patent application Ser. No. 09/291,104, as the male, or pollen, parent. The new Osteospermum was selected by the Inventor as a flowering plant within the progeny of this cross in a controlled environment in Aabyhoj, Denmark, in 1996.

Plants of the new Osteospermum are less spreading, have smaller inflorescences and shorter peduncles than plants of the female parent, the selection 9631. Plants of the new Osteospermum are more compact, have shorter peduncles and have lighter lavender ray florets than plants of the male parent, the cultivar Dondo.

Asexual propagation of the new cultivar by terminal cuttings at Aabyhoj, has shown that the unique features of this new Osteospermum are stable and reproduced true to type in successive generations.

SUMMARY OF THE INVENTION

The following traits have been repeatedly observed and are determined to be the unique characteristics of 'Aksinto'. These characteristics in combination distinguish 'Aksinto' as a new and distinct cultivar:

1. Compact and mounding growth habit.
2. Very uniform plant habit.
3. Freely flowering with numerous inflorescences per plant.
4. Light lavender ray florets and blue purple disc florets.

5. Short peduncles, flowers held just above and beyond the foliage.
6. Good high temperature tolerance.

The new cultivar can be compared to the Osteospermum cultivar Cape Daisy Congo, disclosed in U.S. Plant Pat. No. 10,342. In side-by-side comparisons conducted in Encinitas, Calif., plants of the new cultivar differ from plants of the cultivar Cape Daisy Congo in the following characteristics:

1. Plants of the new Osteospermum have a more compact, mounded and uniform plant habit than plants of the cultivar Cape Daisy Congo.
2. Plants of the Osteospermum have shorter internodes, more leaves and are more freely branching than plants of the cultivar Cape Daisy Congo and are therefore denser and bushier.
3. Plants of the new Osteospermum are much more freely flowering, especially during the summer, than plants of the cultivar Cape Daisy Congo.
4. Plants of the new Osteospermum have a larger disc diameter than plants of the cutivar Cape Daisy Congo.
5. Plants of the new Osteospermum have shorter peduncles than plants of the cultivar Cape Daisy Congo.

The cultivar Aksinto has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Aksinto'.

The photograph at the bottom of the sheet is a close-up view of typical inflorescence buds, individual ray florets, inflorescences and leaves of 'Aksinto' (left) and 'Cape Daisy Congo' (right). Foliage and floret colors in the photographs may appear different from the actual colors due to light reflectance.

DETAILED BOTANICAL DESCRIPTION

The following observations, measurements and values describe plants of the new cultivar grown in Encinitas, Calif., during the spring in a polyethylene-covered greenhouse. During the production period, day temperatures ranged from 16 to 21° C., night temperatures ranged from 10 to 16° C., and light levels were about 4,000 foot-candles. Plants were pinched (terminal apex removed) one time. Measurements and numerical values represent averages for typical flowering plants grown in one-gallon containers with two plants per container; plants used for descriptions and the photographs were about 19 weeks old.

Color references are made to The Royal Horticultural Society Colour Chart except where general terms of ordinary dictionary significance are used.

Botanical classification: *Osteospermum ecklonis* cultivar Aksinto.

Parentage:

*Female, or seed, parent.*—Proprietary selection of *Osteospermum ecklonis* identified as 9631.

*Male, or pollen, parent.*—*Osteospermum ecklonis* cultivar Dondo, disclosed in U.S. Plant Patent application Ser. No. 09/291,104.

Propagation:

*Type.*—By terminal cuttings.

*Time to initiate roots.*—About 10 days at 18° C.

*Time to develop roots.*—About 21 days at 18° C.

*Root description.*—Fibrous.

Plant description:

*Appearance.*—Perennial herbaceous container and garden plant. Compact, round and mounded plant habit; upright to spreading. Very freely branching, about 16 lateral branches developing after pinching; very dense and bushy.

*Crop time.*—From planting rooted cuttings, about 14 to 19 weeks are required to produce a finished, flowering plant in a one-gallon container.

*Vigor.*—Vigorous.

*Plant height, to top of inflorescence plane.*—About 24 cm.

*Plant spread.*—To outer leaves, about 35 cm; to outer inflorescences, about 40 cm.

*Lateral branch description.*—Length: About 7 cm to 13 cm. Diameter: About 4 mm. Internode length: About 1.2 cm. Texture: Glabrous; woody at base. Color: 146B.

*Foliage description.*—Leaves alternate, single. Length, fully expanded leaves, basal: About 4.25 cm. Width, fully expanded leaves, basal: About 8 mm. Shape: Elliptic. Apex: Broadly acute. Base: Attenuate, sessile. Margin: Entire with occasional minute teeth. Aspect: Mostly flat. Texture: Somewhat coarse, tough, glandular; very sparse pubescence on upper surface. Fragrance: Moderately pungent; herb-like. Color: Young foliage, upper surface: 137B. Young foliage, lower surface: 137C. Fully expanded foliage, upper surface: 147A. Fully expanded foliage, lower surface: 147B. Attenuated leaf base: 147B. Venation, upper and lower surfaces: 147B.

Inflorescence description:

*Appearance.*—Daisy-type composite inflorescence form; actinomorphic. Single inflorescences displayed just above or beyond foliage, upright to horizontal on long peduncles arising from leaf axils. Disc and ray florets arranged acropetally on a capitulum. Very freely flowering, typically about 105 opened and opening inflorescences per plant. Inflorescences last about one week. Inflorescences persistent.

*Flowering response.*—Plants flower continuously from April to October in the Northern Hemisphere.

*Fragrance.*—Faint spicy fruit scent.

*Inflorescence size.*—Diameter: About 6.5 cm. Depth (height): About 1.5 cm. Diameter of disc: About 1.2 cm.

*Inflorescence buds* (*at stage of showing color*).—Length: About 1.8 cm. Width: About 1 cm. Shape: Ovoid. Color: 83C.

*Ray florets.*—Length: About 3.5 cm. Width: About 1 cm. Shape: Ligulate. Apex: Broadly acute; very slightly tri-dentate. Base: Attenuate. Margin: Entire. Aspect: Horizontal to upright; slighty reflexing with development. Texture: Smooth, velvety. Number of ray florets per inflorescence: About 24 in two whorls. Color: When opening, upper surface: Base and apex, 77B; midsection, 75B to 75C. When opening, lower surface: Soft alternating longitudinal stripes of 77C to 77D, 74D and 79C. Fully opened, upper surface: 77B to 77C; fading to 75C with subsequent development. Fully opened, lower surface: Ground, 76C, tinged with 74D.

*Disc florets.*—Shape: Tubular; five-lobed, fluted at apex. Number of disc florets per inflorescence: Numerous, about 94. Length: About 9 mm. Width: About 2 mm. Color: Immature: Base, 145D; apex, 93A. Mature: Base, 87B; apex, 93A.

*Phyllaries.*—Shape: Ligulate, narrow. Length: About 1.4 cm. Apex: Acute. Margin: Entire; membranous edges. Quantity and arrangement: About 20 in a single whorl. Color: upper surface, 146C; lower surface, 146A.

*Peduncle.*—Length: Terminal peduncle, about 7 cm; third peduncle, about 10 cm. Aspect: Moderately strong; inflorescences held above foliage. Primary peduncles, about 45° to vertical. Texture: Smooth. Color: 146A.

*Reproductive organs.*—Androecium: Present on disc florets only. Stamens: Five. Anther shape: Elongated, oblong. Anther length: About 3 mm. Anther color: 83A. Pollen amount: Scarce. Pollen color: 23B. Gynoecium: Present on ray and disc florets. Pistils: One. Pistil length: About 9 mm. Stigma shape: Bipartite. Stigma color: 83A. Style length: About 4 mm. Style color: 83C. Ovary color: 145A.

*Seed.*—Seed development has not been observed.

Disease resistance: Resistance to pathogens common to Osteospermum has not been observed on plants of the new Osteospermum.

It is claimed:

1. A new and distinct cultivar of Osteospermum plant named 'Aksinto', as illustrated and described.

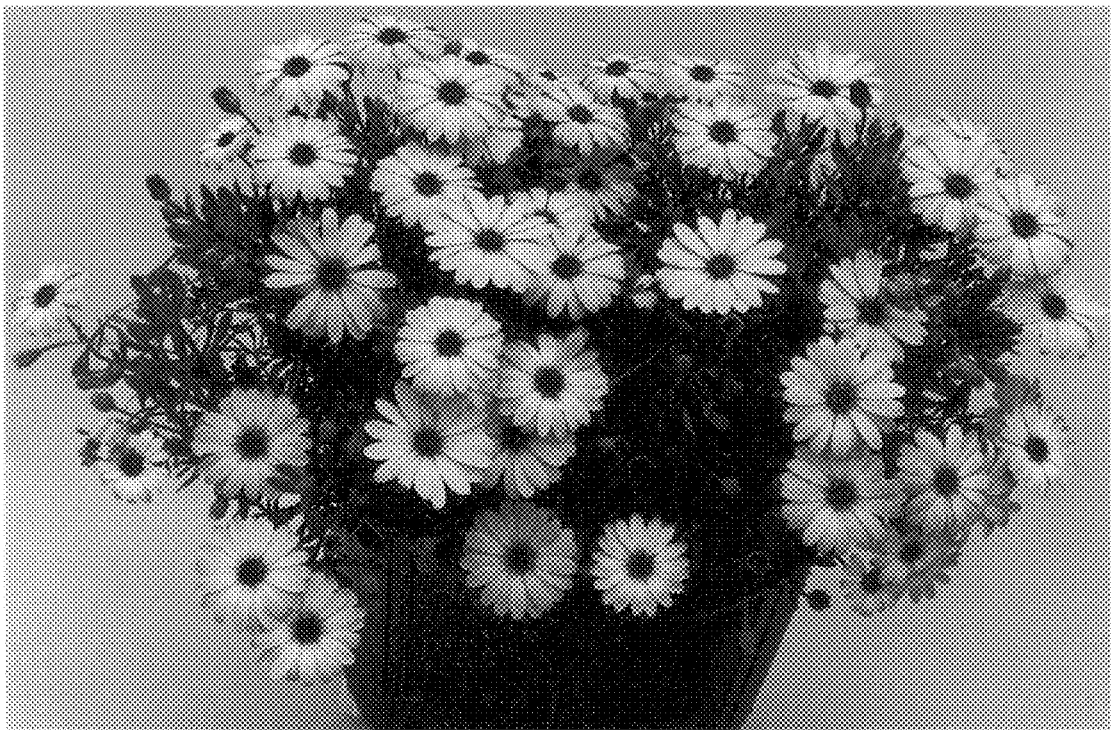
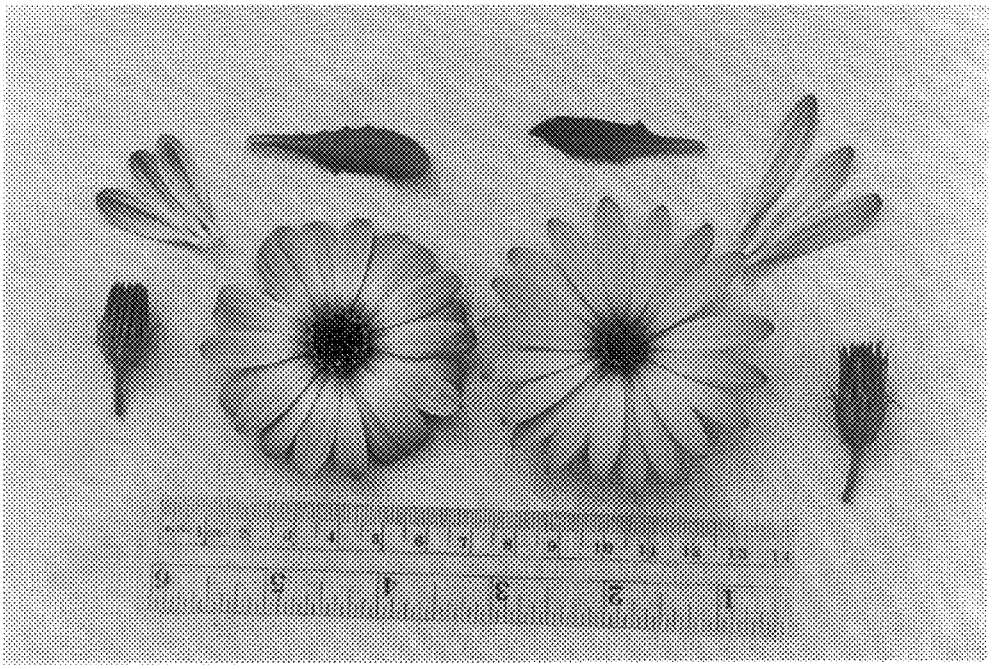

* * * * *